US009970949B1

(12) United States Patent
Hall et al.

(10) Patent No.: US 9,970,949 B1
(45) Date of Patent: May 15, 2018

(54) METHOD FOR IDENTIFYING AND TRACKING PHARMACEUTICAL AND NUTRITIONAL PRODUCTS USING NANOPARTICLES OF DIFFERENT SIZES AND SHAPES

(71) Applicants: David R. Hall, Provo, UT (US); Joe Fox, Spanish Fork, UT (US); Steven J. M. Butala, Provo, UT (US); Dan Allen, Springville, UT (US); Andrew Nguyen, Provo, UT (US); Daniel Hendricks, Provo, UT (US); Terrece Pearman, Draper, UT (US)

(72) Inventors: David R. Hall, Provo, UT (US); Joe Fox, Spanish Fork, UT (US); Steven J. M. Butala, Provo, UT (US); Dan Allen, Springville, UT (US); Andrew Nguyen, Provo, UT (US); Daniel Hendricks, Provo, UT (US); Terrece Pearman, Draper, UT (US)

( * ) Notice: Subject to any disclaimer, the term of this patent is extended or adjusted under 35 U.S.C. 154(b) by 0 days. days.

(21) Appl. No.: 15/612,071

(22) Filed: Jun. 2, 2017

(51) Int. Cl.
| | | |
|---|---|---|
| *G01N 33/94* | (2006.01) |
| *G01N 33/02* | (2006.01) |
| *G01N 33/15* | (2006.01) |
| *G01N 21/00* | (2006.01) |
| *G01N 33/52* | (2006.01) |

(52) U.S. Cl.
CPC ............ *G01N 33/94* (2013.01); *G01N 33/02* (2013.01); *G01N 33/15* (2013.01); *G01N 33/521* (2013.01); *G01N 21/00* (2013.01); *G01N 2458/00* (2013.01); *Y10T 436/13* (2015.01)

(58) Field of Classification Search
CPC ........ G01N 33/02; G01N 33/15; G01N 33/20; G01N 21/00; G01N 21/47; G01N 21/59; G01N 21/65; G01N 33/94; Y10T 436/13
USPC ................ 436/20, 56, 73, 80, 84, 164, 171; 422/82.05, 82.09
See application file for complete search history.

(56) References Cited

U.S. PATENT DOCUMENTS

| | | | | |
|---|---|---|---|---|
| 8,888,005 B2* | 11/2014 | Prokop | ............... | G06F 19/3462 235/440 |
| 2003/0166297 A1* | 9/2003 | Natan | ................... | B22F 1/0018 436/166 |
| 2004/0103043 A1* | 5/2004 | Reade | ................. | G06Q 20/208 705/23 |

(Continued)

*Primary Examiner* — Maureen Wallenhorst

(57) ABSTRACT

We disclose a method of tagging pharmaceutical and nutritional products with nanoparticles which include noble metals. The disclosure describes a plurality of nanoparticles each with either a different size and/or shape. The nanoparticles of different sizes and shapes are distinguishable using spectroscopic techniques because each is associated with different optical properties and have a different spectral signature. The different optical properties are at least due to the unique size or shape of the nanoparticles. Each of the plurality of nanoparticles may be associated with a different characteristic of the tagged pharmaceutical or nutritional product. The method includes mixing the nanoparticles with or adhering the nanoparticles to the tagged pharmaceutical or nutritional product. Two or more of the plurality of nanoparticles may be mixed with or adhered to the tagged pharmaceutical or nutritional product in a ratio and the ratio may be associated with a characteristic of the product.

4 Claims, 9 Drawing Sheets

(56) References Cited

U.S. PATENT DOCUMENTS

| | | | | |
|---|---|---|---|---|
| 2008/0213904 A1* | 9/2008 | Sliwa | ............... | A61B 5/1171 |
| | | | | 436/56 |
| 2009/0084981 A1* | 4/2009 | Bown | ............ | G01N 21/8806 |
| | | | | 250/459.1 |
| 2010/0050901 A1* | 3/2010 | Biris | .................. | B42D 25/29 |
| | | | | 106/31.14 |

* cited by examiner

| Name | Shape | Name | Shape |
|---|---|---|---|
| tetrahedron |  | truncated rhombic dodecahedron | 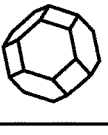 |
| minimally truncated tetrahedron |  | rhombic dodecahedron | 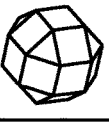 |
| truncated tetrahedron |  | cubo-rhombic dodecahedron | 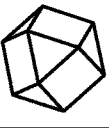 |
| octahedron | 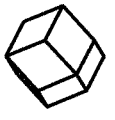 | doubly truncated octahedron |  |
| truncated octahedron | 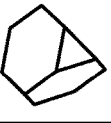 | small rhombicuboctahedron | 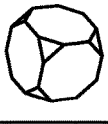 |
| cuboctahedron | 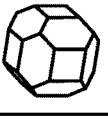 | great rhombicuboctahedron |  |
| truncated cube |  | triangular prism | 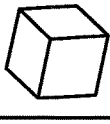 |
| cube | 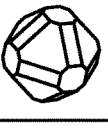 | Marks decahedron | 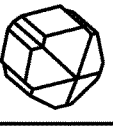 |
| | | regular icosahedron |  |

| Nanoparticle #1 | | Nanoparticle #2 | | Nanoparticle #3 | | Ratio | Active Ingredient |
|---|---|---|---|---|---|---|---|
| shape | diameter | shape | diameter | shape | diameter | | |
| triangular prism | 15 | rod: hexagon cross-section | 20 | cube | 30 | 1:3:2 | vitamin C |
| truncated tetrahedron | 20 | truncated cube | 35 | rod: star-shaped cross-section | 10 | 2:1:5 | ginseng |
| regular icosahedron | 30 | doubly truncated octahedron | 20 | rod: pentagon cross-section | 15 | 3:1:4 | vitamin D3 |
| octahedron | 50 | rod: rectangle cross-section | 25 | cuboctahedron | 10 | 2:3:1 | calcium |

FIG. 7

METHOD FOR IDENTIFYING AND TRACKING PHARMACEUTICAL AND NUTRITIONAL PRODUCTS USING NANOPARTICLES OF DIFFERENT SIZES AND SHAPES

BACKGROUND

Field of the Invention

This disclosure relates to tagging pharmaceutical and nutritional products to identify and distinguish the products.

Background of the Invention

Detecting and verifying consumption of pharmaceutical or nutritional products, is a challenge for managing product distribution, patient treatment, drug abuse, counterfeit products, as well as tracking the sources of foods, nutritional supplements, and food ingredients. Some active ingredients in pharmaceutical or nutritional products are delivered in quantities as small as 10-20 mg or even smaller. These small quantities make direct detection of the active ingredient challenging. Furthermore, many pharmaceutical or nutritional products are metabolized or partially metabolized in the body. Consequently, the concentration of the components of the products and the concentration of metabolic by-products of the components in biological fluids and tissues varies over time making tracking difficult.

Several methods have been used to identify consumed pharmaceutical or nutritional products in bodily waste. These methods include micro-scale consumable bar codes which pass through the digestive tract, unique surface markings, and unique combinations of pill shapes and colors. Detection of these unique features urine or feces is not possible in some cases.

Chemical taggants have been used to a limited degree. These taggants are limited, in part, because they must be biologically inert so that they do not adversely affect the delivery or activity of the active ingredients in medications or nutritional supplements. A taggant optimized for properties such as optical or chemical detectability may not meet these requirements.

A series of taggants that may be added to pharmaceutical or nutritional products, which have a known safety profile, are biologically inert, and which are readily detectable is needed. Ideally, the series of taggants includes a large enough number to identify many data points along the chain of distribution.

Multiple taggants, each of which may provide a different characteristic or piece of information about the pharmaceutical or nutritional products, would be useful. However, it is important for the multiple taggants to be detectably distinct from each other and others in the series. A series of taggants which are biologically inert, detectable in small quantities, and distinguishable from each other is needed.

BRIEF SUMMARY OF THE INVENTION

We disclose a method of manufacturing tagged pharmaceutical and nutritional products using taggants that include noble metal nanoparticles of varying shapes and sizes. The taggants may include a series of different types of noble metal nanoparticles which are detectably distinct from each other at least because of their differing shapes and/or sizes which result in differing optical properties. Thus, the taggants may be measurable and distinguishable by spectroscopic analytical techniques. The taggants may include noble metal nanoparticles which have an aspect ratio of about 1, may be anisotropic, may be rod-shaped, or a combination thereof. Differences in size may result from differences in diameter, width, or both diameter and width. In some embodiments, the taggants may include multiple different types of noble metal nanoparticles provided in defined ratios. In these embodiments, the defined ratios are part of the taggant and associated with characteristics of the tagged pharmaceutical and nutritional product.

The disclosed method includes the steps of providing one or more taggants which include at least one detectably distinct noble metal nanoparticle and providing a pharmaceutical or nutritional product. Each taggant may be associated with a characteristic of the pharmaceutical or nutritional product. The one or more taggants may be adhered to or mixed with the pharmaceutical or nutritional product.

BRIEF DESCRIPTION OF THE DRAWINGS

FIG. 1 is a table which illustrates perspective views of nanoparticles of various shapes which may be used as taggants according to the disclosure.

FIG. 7 is a table illustrating the use of multiple different nanoparticles in defined ratios to identify the main ingredient in a nutritional supplement product.

DETAILED DESCRIPTION OF THE INVENTION

Definitions

Figure 2A:
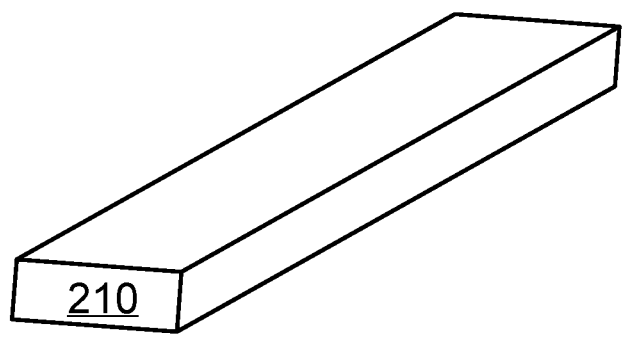
FIGS. 2A, 2B, 2C, 2D, 2E, and 2F illustrate perspective views of rod-shaped nanoparticles which have cross-sections of various shapes and which may be used as taggants according to the disclosure.

Drug, as used herein, means any pharmacologically active agent or mixture of agents. Drug may include one or more placebos.

Nutritional product, as used herein, means a nutritional supplement, food, food ingredient, or any product from which a user may derive nutrients.

Diameter, as used herein, means the distance across the width of the nanoparticle at its widest point.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a method of tagging pharmaceutical or nutritional supplement products, in which nanoparticle taggants are added to the products. The nanoparticles used in the taggants may comprise noble metals. In some embodiments, noble metals may include one or more of gold, silver, copper, platinum, palladium, ruthenium, rhodium, or iridium.

The nanoparticles may be may grouped in one or more series that include multiple detectably distinct types of nanoparticles. The nanoparticles may be detectably distinct at least because of their differing shapes, diameters, lengths, or a combination thereof. For example, both González et al. (González, A. L., Noguez, C., Beránek, J., and Barnard, A. S. Size, Shape, Stability, and Color of Plasmonic Silver Nanoparticles. *J. Phys. Chem. C* 2014, 118, 9128-9136) and Kelley et al. (Kelley, K. L., Coronado, E., Zhao, L. L. and Schatz, G. C. The Optical Properties of Metal Nanoparticles: The Influence of Size, Shape, and Dielectric Environment. *J. Phys. Chem. B* 2003, 107, 668-677) discuss the association of nanoparticles and their sizes and shapes with regard to their optical properties. Accordingly, nanoparticles of different shapes, diameters, and/or lengths may be differentially detected and quantified based on their differing optical properties using spectroscopic techniques. Both González et al. and Kelley et al. are hereby incorporated by reference in their entirety.

In some embodiments, the taggants may include nanoparticles which have an aspect ratio of about one. These may include one or more of the following shapes: tetrahedron, minimally truncated tetrahedron, truncated tetrahedron, octahedron, truncated octahedron, cuboctahedron, truncated cube, cube, truncated rhombic dodecahedron, rhombic dodecahedron, cubo-rhombic dodecahedron, doubly truncated octahedron, small rhombicuboctahedron, great rhombicuboctahedron, triangular prism, Marks decahedron, and regular icosahedron. In other embodiments, the taggants may include anisotropic nanoparticles.

In some embodiments, the taggants may include rod-shaped nanoparticles with profiles or cross-sections of differing shapes. These profiles or cross-sectional shapes may include, but are not limited to, rectangle, hexagon, pentagon, square, triangle, branched, and star-shaped. The rod-shaped nanoparticles may further comprise differing diameters, lengths, or both differing diameters and lengths.

In some embodiments, the nanoparticles include branched shapes, which may include bi-pod, tri-pod, tetra-pod, and multi-pod. These branched shaped nanoparticles may include two-dimensional branched nanoparticles or three-dimensional branched nanoparticles. The branched nanoparticles may also be elongated into branched rod nanoparticles.

In some embodiments may include nanoparticles that have an aspect ratio of about 1, rod-shaped nanoparticles, anisotropic nanoparticles, or combinations thereof. Each type of nanoparticle according to the present disclosure may be included in a series of nanoparticle taggants.

The nanoparticles may also vary in size, which may include variations in length and/or diameter. In some examples, the taggants may include nanoparticles of between about 5 nm and about 150 nm in diameter. In some embodiments, the taggants may include nanoparticles of between about 10 nm and about 50 nm in diameter.

The taggants according to the disclosure may be differentially detectable using spectroscopic analytical techniques. As discussed herein, the different shapes and sizes of the nanoparticles impact their optical properties. Accordingly, in some embodiments, the spectroscopic analytical techniques may include light absorption spectroscopy. In some embodiments, the spectroscopic analytical techniques may include one or more of near infrared spectroscopy, ultraviolet spectroscopy, visible-spectroscopy, ultraviolet-visible spectroscopy, and Raman spectroscopy.

According to an embodiment of the disclosed method, at least one taggant comprising one or more of a series of nanoparticles as disclosed herein and a pharmaceutical or nutritional product are provided. The at least one taggant may be detectably distinct and associated with a characteristic of the pharmaceutical or nutritional product. In some embodiments, the association of the taggant and the characteristic of the pharmaceutical or nutritional product may be recorded and stored in a database. The at least one taggant may be mixed with or adhered to the pharmaceutical or nutritional product.

The nanoparticles may be adhered to the pharmaceutical or nutritional product using a variety of methods known in the art. Nanoparticles may be sprayed on pharmaceutical or nutritional product, included as a dry or liquid ingredient in the pharmaceutical or nutritional product, or dispersed or dissolved in a liquid pharmaceutical product or liquid nutritional product. The nanoparticles may also be dusted on or adhered to pharmaceutical or nutritional products. The pharmaceutical or nutritional products may be dipped in solutions that include the nanoparticles. In an example, the nanoparticles are mixed with the drug or nutritional supplement in powder form before pill or capsule formation so that nanoparticles are difficult to separate from the active ingredient in the drug or nutritional supplement formulation.

In another example, the nanoparticles may be mixed with or adhered to a food ingredient or finished food product using the same or similar techniques described above. For example, the nanoparticles may be mixed with flour to be later used in baked products to identify the source of the flour. In another example, the nanoparticles may be mixed with or adhered to the final baked product to provide information about the final food product.

Characteristics which may be associated with a nanoparticle taggant may include drug product manufacturer, drug, drug composition, drug manufacturing batch, dispensing pharmacy, prescribing healthcare provider, healthcare provider's institution, and prescribed user. Other characteristics which may be associated with a nanoparticle taggant may include a nutritional product manufacturer, nutritional supplement identity, nutritional supplement formulation, food ingredient, food ingredient source, and prepared food product.

In some embodiments, more than one type of nanoparticle may be included in the pharmaceutical or nutritional product. For example, two, three, four, or five detectably different types of nanoparticles may be added to a pharmaceutical or nutritional product. Each type of nanoparticle may be associated with a different characteristic of the product.

Multiple types of nanoparticles may be included in pharmaceutical or nutritional products in defined ratios. In addition to the identities of the multiple types of nanoparticles, their relative ratios may be part of the taggant and associated with specific information about the product. In an example, the product may include two, three, four, or five different types of nanoparticles in defined relative ratios. For example, noodles in a pasta product may be dusted with three different types of detectably different nanoparticles which have different shapes and diameters. The three types of nanoparticles, types 1, 2, and 3, may be present in a ratio of 1:3:2 respectively. Upon detecting the three types of nanoparticles, their identity specifically in a ratio of 1:3:2 may indicate a particular pasta manufacturer. Alternatively, another product may include nanoparticles types 1, 2, and 3 but in a different ratio. This other product therefore includes a different taggant due to the different ratios of nanoparticles types 1, 2, and 3. In another example, each of nanoparticles types 1, 2, and 3 may be associated with a characteristic of the product and the ratio of the three may be associated with another characteristic of the product. For example, nanoparticle type 1 may be associated with an active ingredient in a pharmaceutical product, nanoparticle type 2 may be associated with the pharmaceutical product's manufacturer, and nanoparticle type 3 may be associated with a formulation. The ratio of the three types of nanoparticles at 1:3:2 may indicate the batch the product was part of when it was manufactured.

Similar to the taggants which do not include relative ratios of different nanoparticles, the taggants which include nanoparticles at defined ratios may be associated with characteristics about the product which may include a drug product, drug manufacturer, drug, drug composition, manufacturing batch, dispensing pharmacy, prescribing healthcare provider, healthcare provider's institution, and prescribed user. The characteristics may also include a nutritional product manufacturer, nutritional supplement identity, nutritional supplement formulation, food ingredient, food ingredient source, and prepared food product.

Referring now to the Figures, FIG. 1 illustrates examples of nanoparticles of various shapes which may be used to perform the disclosed method. These are non-spherical shapes which may also vary in their diameter. For example, one nanoparticle may be the shape of an octahedron with a 10 nm diameter and another nanoparticle may be the shape of an octahedron with a 50 nm diameter. The shapes illustrate in FIG. 1 include a tetrahedron, a minimally truncated tetrahedron, a truncated tetrahedron, an octahedron, a truncated octahedron, a cuboctahedron, a truncated cube, a cube, a truncated rhombic dodecahedron, a rhombic dodecahedron, a cubo-rhombic dodecahedron, a doubly truncated octahedron, a small rhombicuboctahedron, a great rhombicuboctahedron, a triangular prism, a Marks decahedron, and a regular icosahedron. The shapes shown in FIG. 1 are examples and are not meant to limit the shapes which the disclosure encompasses.

Figure 2B:
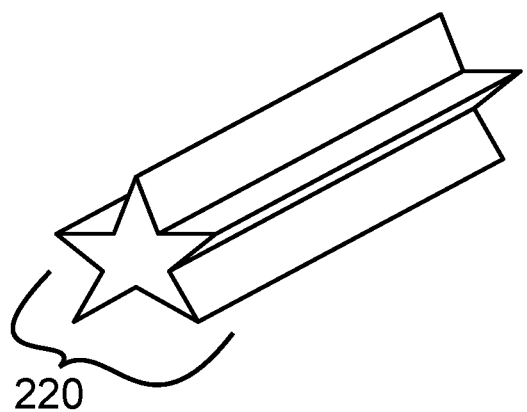
Figure 2C:
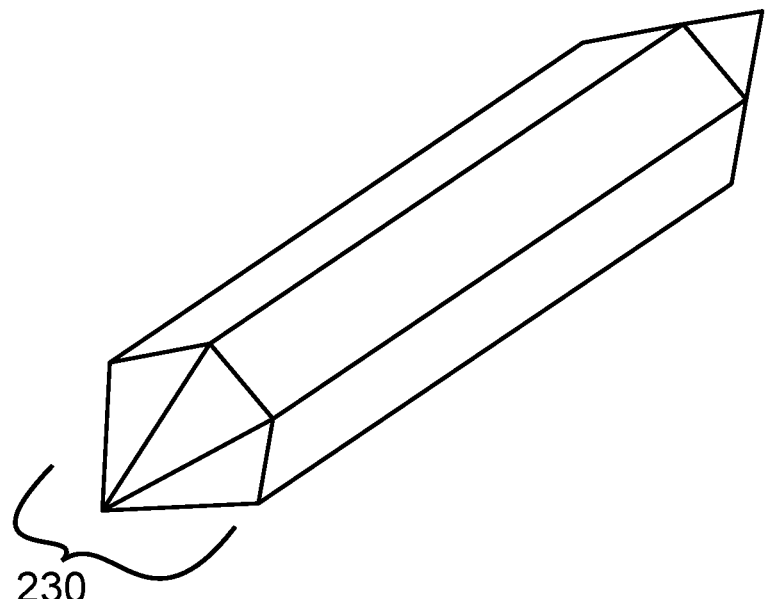
Figure 2D:
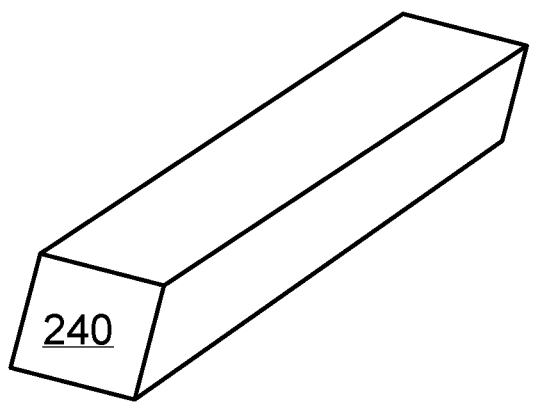
Figure 2E:
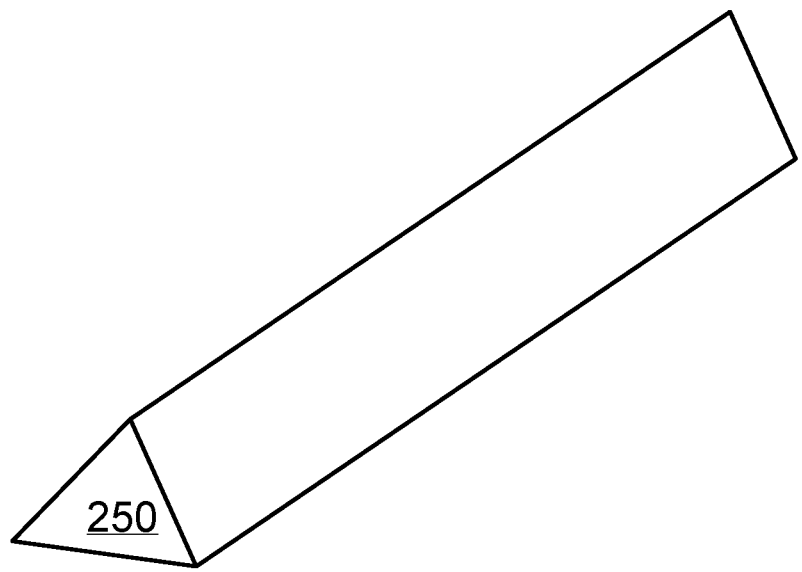
Figure 2F:
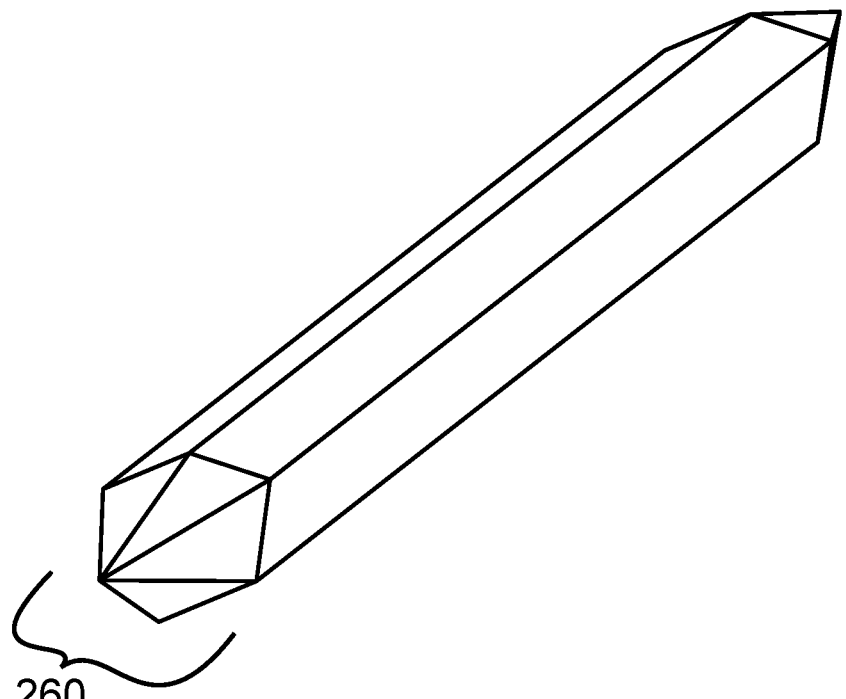

FIG. 2A-F illustrate examples of rod-shaped nanoparticles which may be used when performing the disclosed method. Each example has a different shaped cross-section. FIG. 2A shows a rod-shaped nanoparticle with rectangle cross-section 210. FIG. 2B shows a rod-shaped nanoparticle with star-shaped cross-section 220. FIG. 2C shows a rod-shaped nanoparticle with five triangular faces 230 on its near end. Though not visible in the drawing, the example of FIG. 2C includes five triangular faces on the far end. The cross-sectional view of the example in FIG. 2C is a pentagon. FIG. 2D shows a rod-shaped nanoparticle with square cross-section 240. FIG. 2E shows a rod-shaped nanoparticle with triangle cross-section 250. FIG. 2F shows a rod-shaped nanoparticle with six triangular faces 260 on its near end. Though not visible in the drawing, the far end includes six triangular faces. The cross-section of the view of the example in FIG. 2F is a hexagon. The shapes of the rod-shaped nanoparticles shown in FIGS. 2A-F are examples and are not meant to limit the shapes which the disclosure encompasses. The nanoparticles of FIGS. 2A-F may comprise different diameters and lengths from end to end. For example, a nanoparticle of the shape shown in FIG. 2E with triangle shaped cross-section 250 may include a diameter of 30 nm and a length of 100 nm while another nanoparticle may also comprise the shape of FIG. 2E but with a diameter of 40 nm and a length of 60 nm.

Figure 3:
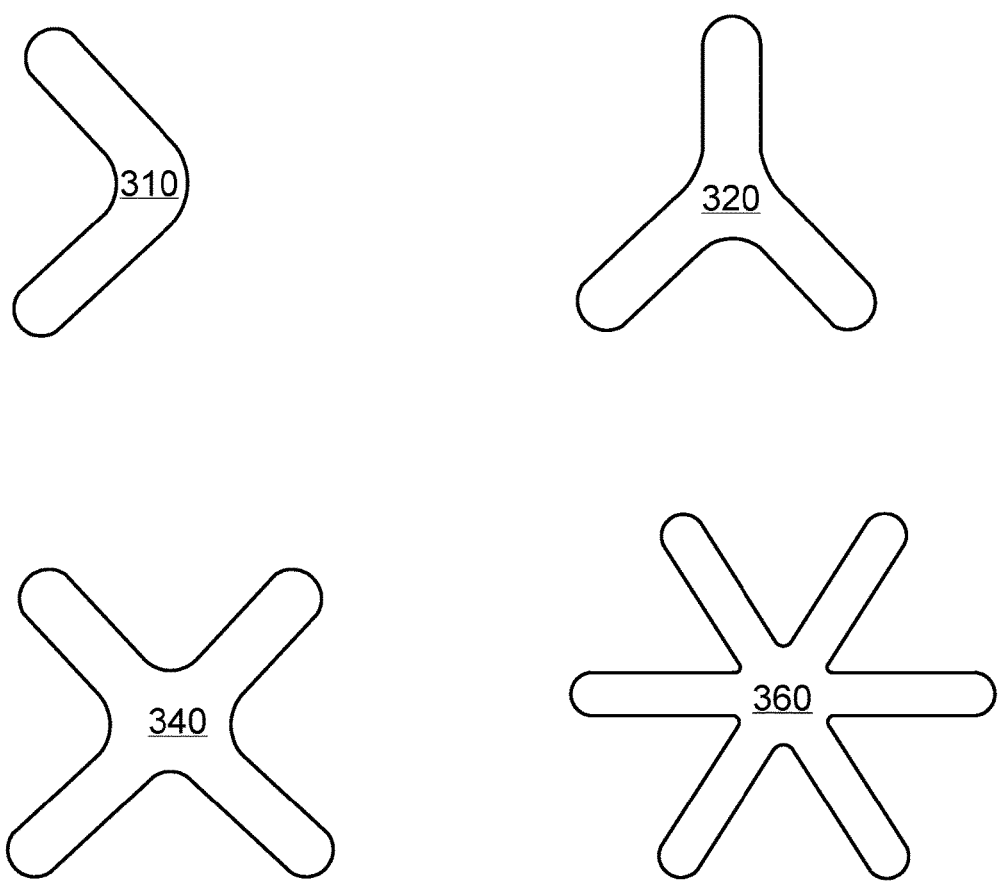
FIG. 3 illustrates embodiments of branched shaped nanoparticles which may be used as taggants according to the disclosure.

FIG. 3 illustrates examples of branched nanoparticles of various shapes which may be used according to the disclosed method. These include bi-pod nanoparticle 310, tri-pod nanoparticle 320, tetra-pod nanoparticle 340, and hexa-pod nanoparticle 360. Branched nanoparticles may include the same number of pods but have different diameters. For example, the series of nanoparticles may include a bi-pod nanoparticle with a 30 nm diameter and a bi-pod nanoparticle with a 70 nm diameter. While FIG. 3 illustrates two-dimensional branched nanoparticles, three-dimensional branched nanoparticles and elongated, branched rod nanoparticles are within the scope of the disclosure.

Figure 4:
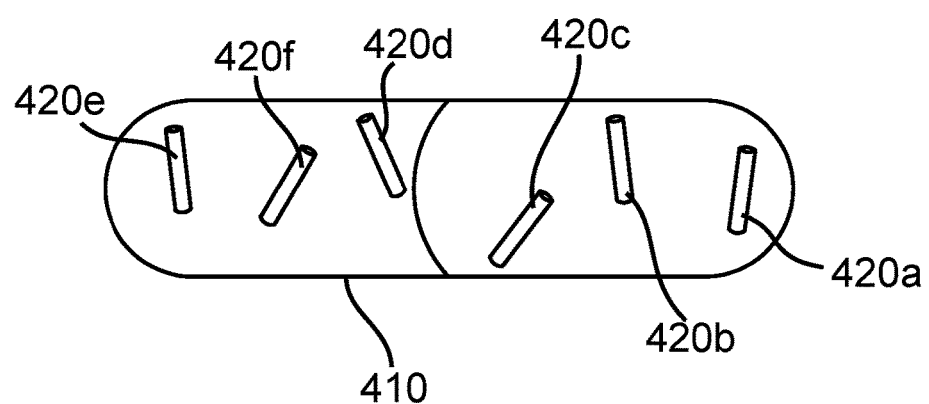
FIG. 4 illustrates a perspective view of a capsule with rod-shaped nanoparticles adhered to its surface.

FIG. 4 illustrates capsule 400 which has been manufactured according to an embodiment of the disclosed method. Capsule 400 includes a powdered formulation which includes a drug inside its shell 410. Rod-shaped nanoparticles 420a, 420b, 420c, 420d, 420e, and 420f have been adhered to the outside surface of shell 410 of capsule 400 either before or after loading shell 410. For clarity, the relative size of nanoparticles 420a-f and shell 410 are not accurate.

Figure 5A:
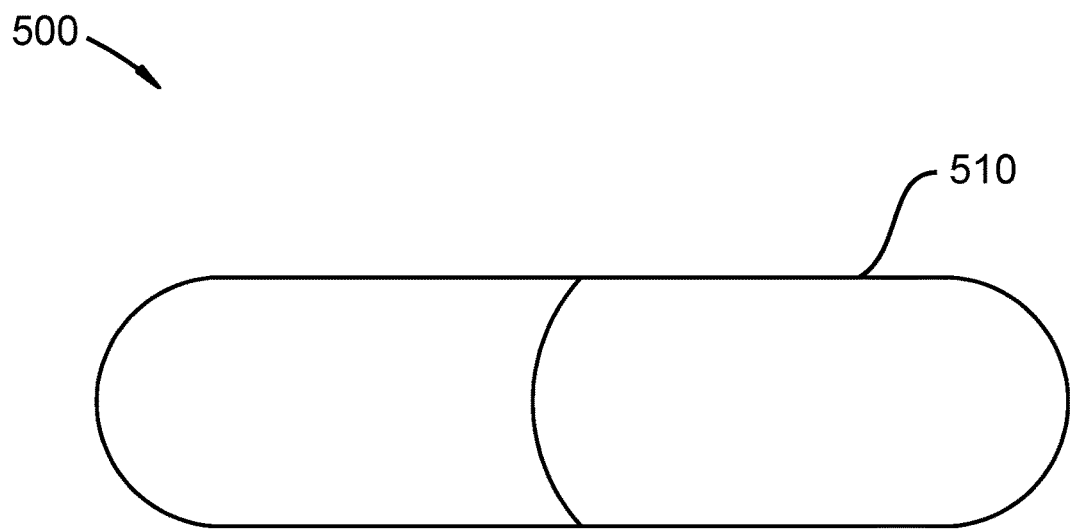
FIG. 5A illustrates perspective view of a capsule in which nanoparticles according to the disclosure have been mixed with a powdered drug formulation prior to loading the capsule.

FIG. 5A illustrates capsule 500 which has been manufactured according to an embodiment of the disclosed method. Capsule 500 contains a drug formulation inside its shell 510. Unlike capsule 400 of FIG. 4, the nanoparticles have not been adhered to the outside surface of capsule 500. Rather, rod-shaped nanoparticles were mixed with the drug formulation prior to loading the drug formulation into shell 510.

Figure 5B:
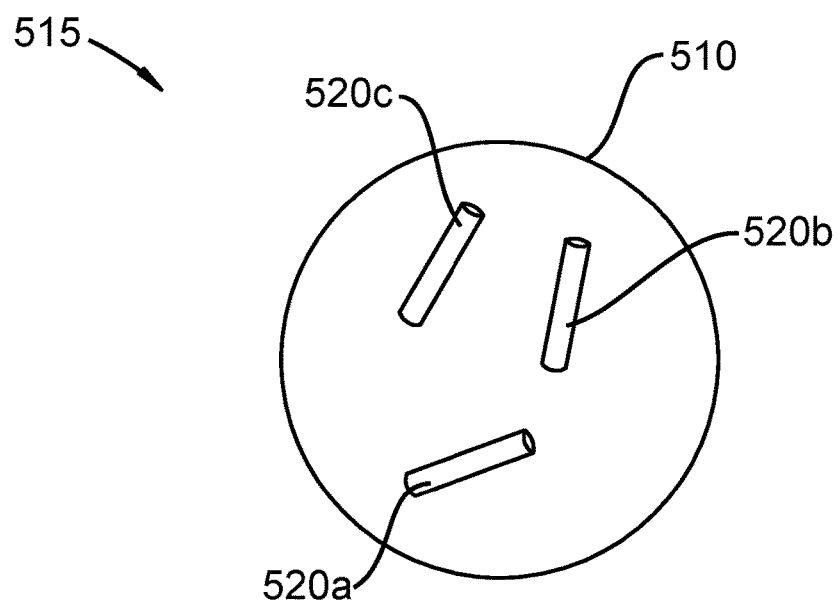
FIG. 5B illustrates a cross-sectional view of the capsule of FIG. 5A showing the rod-shaped nanoparticles inside.

FIG. 5B illustrates a cross-sectional view of capsule 500. Nanoparticles 520a-c are shown mixed in with the drug formulation which comprises the contents of capsule 500. For clarity, the relative size of nanoparticles 520a-c and shell 510 are not accurate.

Figure 6:
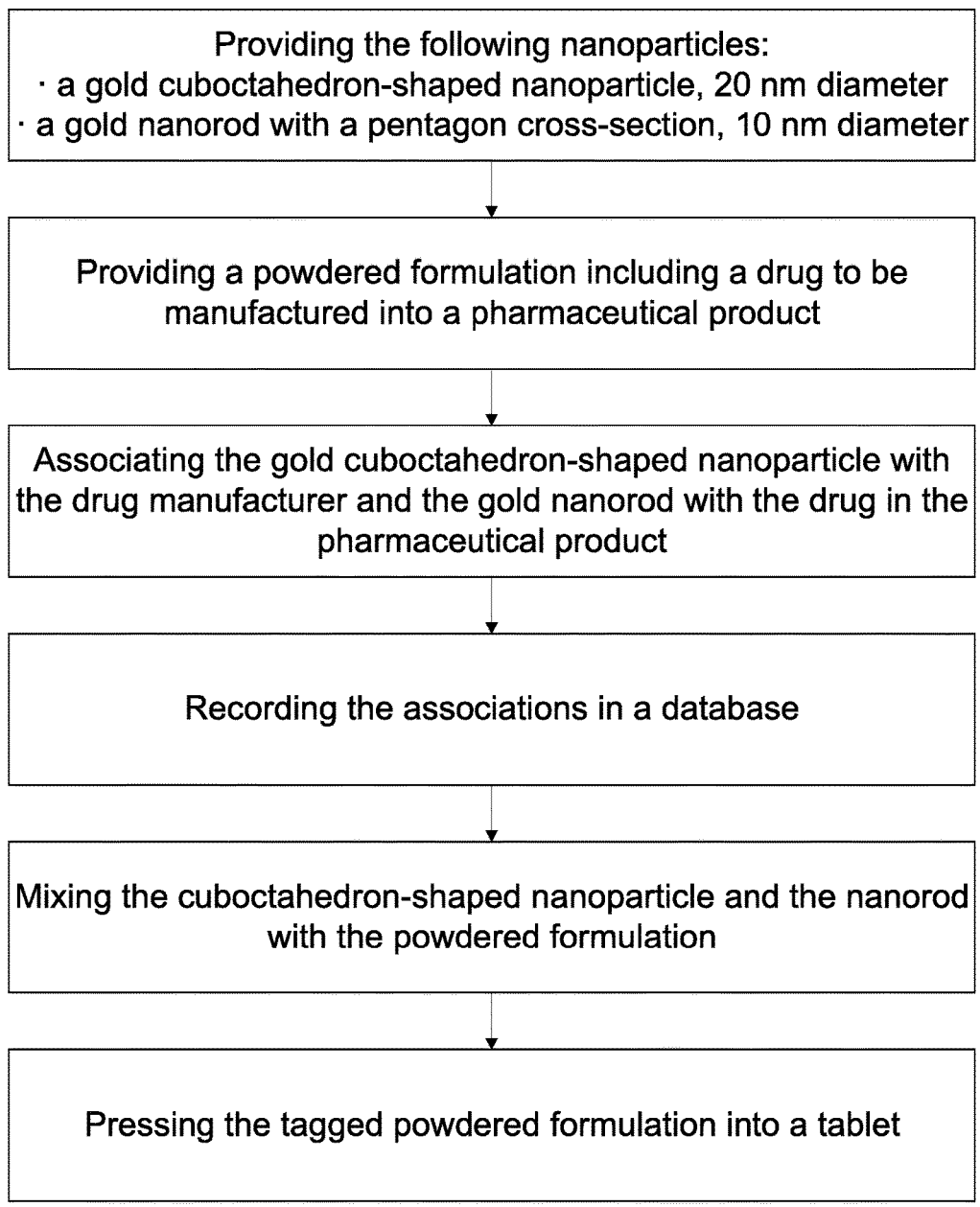
FIG. 6 is a flow chart illustrating steps for performing an embodiment of the disclosed method.

FIG. 6 is a flow chart which illustrate steps which may be performed according to the disclosed method. The embodiment of shown in FIG. 6 begins with providing two types of nanoparticles from a series. These include a gold cuboctahedron-shaped nanoparticle with a diameter of 20 nm and a gold rod-shaped nanoparticle (a nanorod) which has a pentagon cross-section and a diameter of 10 nm. Both nanoparticles may be as shown in FIGS. 1 and 2 respectively. A powdered formulation including a drug which will be used to manufacture a pharmaceutical product is also provided. Each nanoparticle is associated with a characteristic of the pharmaceutical product to be manufactured. Specifically, the gold cuboctahedron-shaped nanoparticle is associated with the drug manufacturer and the gold rod-shaped nanoparticle is associated with the identity of the drug in the pharmaceutical product. The nanoparticles and the associated characteristics are entered and stored in a database for future use. Both nanoparticles are mixed with the powdered drug formulation. The tagged drug formulation is then pressed into pills which may be consumed by a patient.

FIG. 7 is a table illustrating the use of multiple different nanoparticles in defined ratios to identify the main ingredient in a nutritional supplement product. In the embodiment of FIG. 7, each nutritional supplement product is tagged with three different types of nanoparticles. The three types of nanoparticles in each nutritional supplement product differ by both shape and diameter. In addition, the three types of nanoparticles are provided in defined ratios as shown in the table. In addition to the types of nanoparticles, the ratios in which they are present in the nutritional supplement product are part of the taggant. Both the identities of the three types of nanoparticles and the relative ratios in which they are provided are associated with a different active ingredient.

The active ingredients in the products shown in FIG. 7 include vitamin C, ginseng, vitamin D3, and calcium.

While specific embodiments have been described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method for tagging a pharmaceutical or nutritional product comprising the steps of:
   a. providing at least two of a plurality of noble metal nanoparticles, wherein each of the at least two of the plurality of noble metal nanoparticles comprises a defined diameter and shape, and wherein each of the at least two of the plurality of noble metal nanoparticles comprises a unique optical spectrum;
   b. associating a characteristic of the pharmaceutical or nutritional product with each of the at least two of the plurality of noble metal nanoparticles;
   c. associating a characteristic of the pharmaceutical or nutritional product with a ratio of the at least two of the plurality of noble metal nanoparticles; and
   d. mixing or adhering the at least two of the plurality of noble metal nanoparticles with or to the pharmaceutical or nutritional product in the ratio.

2. The method of claim 1, wherein the at least two of the plurality of noble metal nanoparticles comprises three of the plurality of noble metal nanoparticles.

3. The method of claim 1, wherein the step of associating a characteristic of the pharmaceutical or nutritional product with a ratio comprises associating the ratio with a characteristic which is independently selected from the following group: drug product manufacturer, drug, drug composition, manufacturing batch, dispensing pharmacy, prescribing healthcare provider, healthcare provider's institution, and prescribed user.

4. The method of claim 1, wherein the step of associating a characteristic of the pharmaceutical or nutritional product with a ratio comprises associating the ratio with a characteristic which is independently selected from the following group: nutritional product manufacturer, nutritional supplement identity, nutritional supplement formulation, food ingredient, food ingredient source, and prepared food product.

* * * * *